US009677044B2

(12) United States Patent
Botma et al.

(10) Patent No.: US 9,677,044 B2
(45) Date of Patent: Jun. 13, 2017

(54) METHOD FOR PICKING UP CELL MATERIAL AND ASSEMBLY FOR PERFORMING SAID METHOD

(71) Applicant: KIESTRA LAB AUTOMATION DRACHTEN B.V., JC Drachten (NL)

(72) Inventors: Jetze Botma, Drachster Compagnie (NL); Martijn Kleefstra, Dokkum (NL); Martijn Xander Berntsen, Leeuwarden (NL); Tino Walter Van Der Zee, Wiuwert (NL)

(73) Assignee: BD Keistra B.V. (NL)

( * ) Notice: Subject to any disclaimer, the term of this patent is extended or adjusted under 35 U.S.C. 154(b) by 204 days.

(21) Appl. No.: 14/347,841

(22) PCT Filed: Sep. 28, 2012

(86) PCT No.: PCT/NL2012/050681
§ 371 (c)(1),
(2) Date: Mar. 27, 2014

(87) PCT Pub. No.: WO2013/048249
PCT Pub. Date: Apr. 4, 2013

(65) Prior Publication Data
US 2014/0242570 A1    Aug. 28, 2014

(30) Foreign Application Priority Data
Sep. 29, 2011    (EP) .................................... 11183251

(51) Int. Cl.
C12M 1/00      (2006.01)
C12M 1/26      (2006.01)
G01N 35/10     (2006.01)

(52) U.S. Cl.
CPC ............ *C12M 47/02* (2013.01); *C12M 33/00* (2013.01); *G01N 35/1011* (2013.01)

(58) Field of Classification Search
None
See application file for complete search history.

(56) References Cited

U.S. PATENT DOCUMENTS

| 4,613,573 | A  | 9/1986  | Shibayama et al. |
| 5,648,727 | A  | 7/1997  | Tyberg et al. |
| 8,180,575 | B2 | 5/2012  | Esteban et al. |
| 2003/0179916 | A1 | 9/2003 | Magnuson et al. |
| 2005/0026221 | A1 | 2/2005 | Richmond et al. |
| 2008/0019878 | A1 | 1/2008 | Trump |
| 2008/0312843 | A1 | 12/2008 | Esteban et al. |

FOREIGN PATENT DOCUMENTS

| EP | 0277789 A2   | 8/1988 |
| EP | 0941477 A1   | 9/1999 |
| EP | 1502649 A1   | 2/2005 |
| EP | 1602892 A1   | 12/2005 |
| EP | 1754537 A1   | 2/2007 |
| EP | 2025744 A1   | 2/2009 |
| JP | S62273429 A  | 11/1987 |
| JP | S64-67200 A  | 3/1989 |
| JP | 2011103779 A | 6/2011 |
| JP | 2012073197 A | 4/2012 |
| WO | 2005085412 A2 | 9/2005 |

OTHER PUBLICATIONS

Arlett et al., Comparative advantages of mechanical biosensors, Nature Nanotechnology, vol. 6, Apr. 2011.*
Euiwon Bae et al., System automation for a bacterial colony detection and identification instrument via forward scattering; Measurement Science and Technology; IOP Publishing; Meas. Sci. Technol.. 20 (2009) 015802 (9pp).
Heiko Kerkmann, Differentielle Interaktionen hochpotenter Lokalanasthetika mit TTX-sensitiven und TTX-resistenten Natriurnstrornen an Spinalganglienzellen der erwachsenen Ratte, VVB Laufersweiler Verlag, edition scientifique, 2005.
Niels Fertig et al., "Whole Cell Patch Clamp Recording Performed on a Planar Glass Chip", Biophysical Journal vol. 82 Jun. 2002 3056-3062.
International Search Report—PCT/NL2012/050681—Mailing date: Dec. 18, 2012.
Jones P et al: "Integration of Image Analysis and Robotics Into a Fully Automated Colony Picking and Plate Handling System", Nucleic Acids Research, Oxford University Press, Surrey, GB, vol. 20, No. 17, Jan. 1, 1992 (Jan. 1, 1992).
Uber D C et al: "Application of Robotics and Image Processing to Automated Colony Picking and Arraying", Biotechniques, Natick, MA, US, vol. 11, No. 5, Jan. 1, 1991 (Jan. 1, 1991).
www://outsourcing-pharma.com, dated on Feb. 25, 2005 , pp. 1-3 (printed on Jul. 18, 2013).
Life Science Robotics, Microlab® Star Line, Hamilton, 2004, pp. 1-18.
"Hamilton launches Automated Cloning System", BioPharma-Reporter.com [online], Feb. 28, 2005 uploaded, [retrieved Mar. 31, 2016], internet <URL:http://www.biopharma-reporter.com/Downstream-Processing/Hamilton-launches-Automated-Cloning-System>.

* cited by examiner

*Primary Examiner* — Suzanne M Noakes
*Assistant Examiner* — Stephen Chong
(74) *Attorney, Agent, or Firm* — Lerner, David, Littenberg, Krumholz & Mentlik, LLP

(57) ABSTRACT

In a method for picking up cell material from a culture dish a picking tool is displaced towards the cell material. Contact between the tool and the cell material is determined by carrying out capacitive measurements. After contact the tool is removed from the cell material. In an assembly for performing said method a support made of electrically conducting material supports the dish. A measurement device determines the start electrical capacity of the system composed of picking tool and support in a starting position of the tool, and determines the electrical capacity of the system when lowering the tool towards the dish. The measurement device provides signals representing the electrical capacity to a controller, which comprises a comparator for performing a comparison of the electrical capacity during lowering of the tool with the start electrical capacity. The controller controls the positioning of the tool at least based on this comparison.

5 Claims, 1 Drawing Sheet

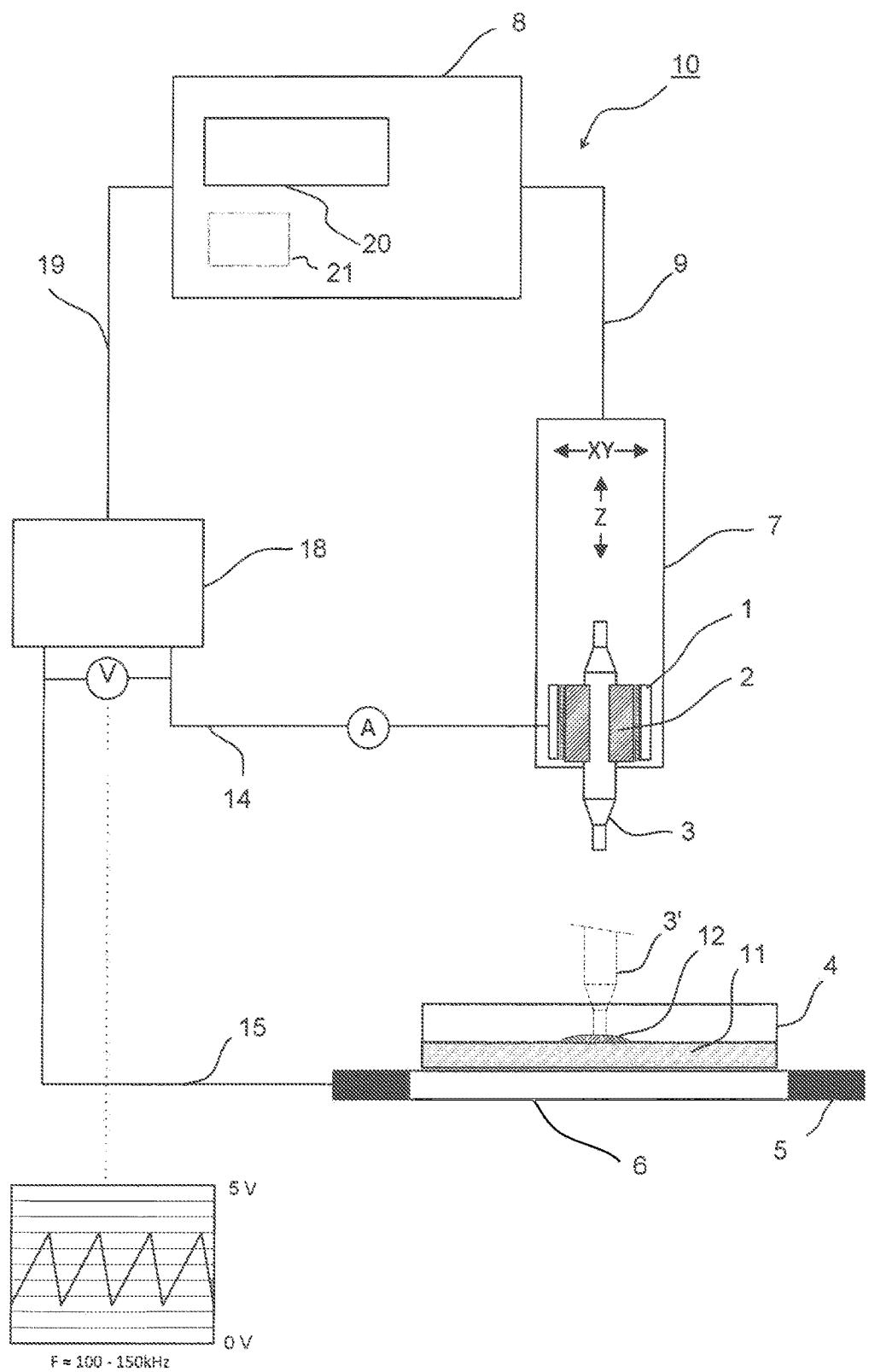

METHOD FOR PICKING UP CELL MATERIAL AND ASSEMBLY FOR PERFORMING SAID METHOD

CROSS-REFERENCE TO RELATED APPLICATIONS

This application is a U.S. National Stage application under 35 U.S.C. §371 of International Application PCT/NL2012/050681 (published as WO 2013/048249 A1), filed Sep. 28, 2012, which claims priority to Application EP 11183251.5, filed Sep. 29, 2011. Benefit of the filing date of each of these prior applications is hereby claimed. Each of these prior applications is hereby incorporated by reference in its entirety.

BACKGROUND OF THE INVENTION

The invention relates to a method for picking up cell material from the surface of a culture medium in a culture dish.

Such a method is known from JP-A-62273429. This known method is related to obtaining a constant needling depth by using a transplanting needle as an electrode and detecting contact between the transplanting needle and a culture medium by an electric signal. An electrode is positioned over the culture medium and then the transplanting needle is lowered to the culture medium. A power supply and a variable resistor are connected to the electrode and the transplanting needle by a lead wire. Since the culture medium has high moisture content, the presence or absence of conduction can be detected by a detector and a detection threshold can be changed by adjusting the variable resistor. A problem that might arise when using this known method is that although a constant needling depth can be obtained it sometimes appears that the transplanting needle has picked up a mixture of cell material and of culture medium below the cell material. In addition the power supply connected to the electrode and the transfer needle produces a current through the culture medium that can be detrimental for the cell material on the culture medium. In addition when changing towards a different culture dish the electrode has to be replaced or thoroughly cleaned to prevent cross-contamination.

SUMMARY OF THE INVENTION

It is an object of the invention to provide a method for picking up cell material from the surface of a culture medium in a culture dish in which the cell material can be selectively picked up.

It is a further object of the invention to provide a method for picking up cell material which is not detrimental for the cell material.

It is a further object of the invention to provide a method for picking up cell material using as less device parts as possible.

At least one of these objects or at least a part thereof is achieved by the invention by providing a method for picking up cell material from the surface of a culture medium in a culture dish, said method subsequently comprising the steps of:
  displacing a picking tool towards the cell material,
  determining contact between the picking tool and the cell material, and
  removing the picking tool from the cell material thereby picking up cell material, wherein the step of determining contact between the picking tool and the cell material is performed by carrying out capacitive measurements. Since contact is determined by carrying out capacitive measurements no additional electrode to be brought directly into contact with the culture medium is necessary to determine contact between picking tool and cell material and/or culture medium. Furthermore, by using capacitive measurements superficial contact is sufficient to determine contact so that the picking tool need not penetrate at all into the cell material to establish contact, thereby making it possible to only pick up cell material. In addition, the voltage levels needed to effect such a measurement are sufficiently low not to induce any harmful effects on the growth of cell material.

A very accurate method according to the invention is provided in case the method comprises the steps of:
  placing the culture dish on a support made of electrically conducting material;
  using a culture dish made of electrically insulating material;
  using a picking tool made of electrically conducting material;
  placing the picking tool in a starting position well above the culture dish;
  measuring the start electrical capacity of the system composed of picking tool and support in the starting position of the picking tool;
  lowering the picking tool from the starting position in a direction towards the culture dish;
  measuring the electrical capacity of the system composed of picking tool and support during lowering of the picking tool.

Preferably the method further comprises the step of stopping the lowering of the picking tool in a contact position when the measured capacity deviates from the start electrical capacity. This prevents that the picking tool is lowered too much, so that it can be prevented to pick up culture medium which is present below the cell material. Preferably the method further comprises the step of measuring the contact position of the picking tool when the measured capacity deviates from the start electrical capacity.

In an advantageous embodiment of a method according to the invention the method further comprises the steps of removing the picking tool a predetermined distance away from the contact position towards a check position and holding said picking tool in said check position and of measuring the electrical capacity of the system composed of picking tool and support in the check position. In some cases cell material to be picked up is very sticky or slimy. When the picking tool after making contact with such a cell material is removed away from the cell material sometimes a thin thread remains in contact between the picking tool and the cell material in the culture dish. This thin thread can break and possibly contaminate the picking tool device. By measuring the electrical capacity in the check position, which for example can be a few millimeters above the culture dish, it is possible to detect the presence of such a thread so that appropriate actions can be taken. Especially when in an embodiment of a method according to the invention in which a picking tool holder is provided for removably holding a picking tool, said picking tool holder being adapted to grasp and release a picking tool it is possible to automate such an action in case of detection of a remaining thread. Preferably the method then comprises the step of releasing the picking tool from the picking tool holder in case the electrical capacity measured in the check position differs from the start electrical capacity such that the picking tool falls into the culture dish, and optionally the step of discarding the culture dish. These steps can easily be performed in an automated way so that no time consuming human intervention is necessary to discard the culture dish.

In an embodiment of a method according to the invention in which the method comprises the step of providing as a support made of electrically conducting material an annular element of electrically conducting material and the step of interposing an element or layer of transparent electrically insulating material between the support and the culture dish, it is possible to provide illumination from below the culture dish to assist in determining the position of cell material in the culture dish.

Preferably the method comprises the step of using a picking tool made of an electrically conductive plastic material, such that the picking tool can be disposable. Although it is possible to thoroughly clean a picking tool after it has picked up cell material and before it is used to pick up further cell material, it is according to an embodiment of a method according to the invention preferable to use a new picking tool each time cell material has to be picked up from the surface of a culture medium in a culture dish. In this way a reliable, cheap and fast way of picking up cell material from a culture dish can be realized.

The invention also relates to an assembly for performing the method for picking up cell material from the surface of a culture medium in a culture dish as claimed in any one of the preceding claims, said assembly comprising:

a picking tool device comprising a picking tool holder of electrically conducting material, said picking tool holder being mounted to the picking tool device in an electrically insulated manner, said picking tool holder holding a picking tool made of electrically conducting material, said picking tool being held by the picking tool holder in an electrically conducting manner;

a culture dish made of electrically insulating material;

a support made of electrically conducting material for supporting the culture dish;

a positioning device for positioning the picking tool in a starting position above the culture dish and for lowering and raising the picking tool towards and away from the culture dish, respectively;

a controller for controlling the movement of the positioning device;

a measurement device for carrying out capacitive measurements for determining the electrical capacity of the system composed of picking tool and support, said measurement device being adapted for determining the start electrical capacity of the system composed of picking tool and support in the starting position of the picking tool and for providing a signal representing the start electrical capacity to the controller, said measurement device being adapted for determining the electrical capacity of the system composed of picking tool and support when lowering the picking tool towards the culture dish and for providing a signal representing the measured electrical capacity to the controller;

said controller comprising a comparator for performing a comparison of the electrical capacity during lowering of the picking tool with the start electrical capacity and for providing a comparison signal indicative of said comparison, said controller controlling the movement of the positioning device at least based on the comparison signal.

Preferred embodiments of the assembly according to the invention are described in the dependent assembly claims.

Further objects, aspects, effects and details of the invention are described in the following detailed description of a number of exemplary embodiments, with reference to the drawings.

BRIEF DESCRIPTION OF THE DRAWINGS

FIG. 1 is a schematic representation of an assembly for performing a method for picking up cell material from the surface of a culture medium in a culture dish according to the invention.

DETAILED DESCRIPTION

FIG. 1 is a schematic representation of an assembly for performing a method for picking up cell material from the surface of a culture medium in a culture dish according to the invention.

The assembly comprises a picking tool device 1 comprising a picking tool holder 2 of electrically conducting material. The picking tool holder 2 is mounted to the picking tool device 1 in an electrically insulated manner. The picking tool holder 2 is adapted for holding a picking tool 3 made of electrically conducting material in an electrically conducting manner. The picking tool 3 can be made of a metal but can also be made of an electrically conductive plastic material, e.g. a plastic comprising carbon.

Furthermore the assembly according to the invention comprises a culture dish 4 made of electrically insulating material, such as glass or an electrically insulating plastic. The culture dish 4 contains a culture medium 11 on which cell material 12 such as a bacteria colony 12 is present. The culture dish 4 is supported on a support 5 made of electrically conducting material. The culture dish 4 may be directly supported in the electrically conductive support 5 or indirectly by interposing an element or layer of electrically insulating material between culture dish 4 and support 5. In the embodiment shown in FIG. 1 the support 5 is an annular element of electrically conducting material, surrounding a layer 6 of transparent electrically insulating material on which the culture dish 4 can be supported. In this manner it is possible to provide illumination from below the culture dish 4 to assist in determining the position of cell material in the culture dish 4. Please note that the layer 6 could in an alternative embodiment also be placed on top of the annular support 5.

A positioning device 7 is arranged for positioning the picking tool 3 (and the picking tool holder 2) in a starting position above the culture dish 4. This positioning device 7 can lower and raise the picking tool 3 towards and away from the culture dish, respectively, under control of a controller, such as a microprocessor 8 or any other suitable means for controlling the operation of the positioning device. In addition the positioning device 7 can displace the picking tool 3 in a plane parallel to the plane of the culture dish 4. The displacements are schematically indicated in FIG. 1 by means of the double headed arrows XY and Z. The microprocessor 8 is connected to the positioning device 7 by means of a signal line 9 in order to properly control the positioning device 7.

The assembly shown in FIG. 1 further comprises a measurement device 10 for detecting or measuring when the picking tool 3 contacts the cell material 12 or the culture medium 11. The measurement device 10 can carry out capacitive measurements for determining the electrical capacity of the system composed of picking tool 3 and support 5. In the embodiment shown in FIG. 1 the measurement device 10 is composed of an oscillator circuit 18, which also functions as an alternating voltage source, which is connected with an electrical lead 14 to the picking tool holder 2 and with another electrical lead 15 to the annular support 5. In the embodiment the oscillator circuit 18 provides a voltage having a value between about 1.25 and about 3.5 V, having a fixed frequency which can be chosen in the range between 100 and 150 kHz. The alternating voltage V provided is a saw-tooth voltage as is schematically shown in the graph in FIG. 1.

The oscillator circuit 18 can for example comprise an operational amplifier multivibrator oscillator. The oscillation frequency of the oscillation circuit is dependent on the value of the electrical capacity of the measuring circuit composed of electrical lead 14, picking tool holder 2, picking tool 3, cell material and/or culture medium 11, culture dish 4, insulating element/layer 6, annular support and electrical lead 15. In case the picking tool 3 is separated from the cell material 12 (shown in solid lines in FIG. 1) the electrical capacity is furthermore determined by the air column present between the picking tool 3 and the cell material 12 and/or culture medium 11. This air column is not present when the picking tool 3' is in contact with the cell material 12 and/or culture medium 11, as is shown with broken lines in FIG. 1. The oscillator circuit 18 is connected to the microprocessor 8 via a measuring line 19. The microprocessor comprises in the shown embodiment a display 20 for displaying measuring results.

Thus the measurement device 10 can determine the start electrical capacity of the system composed of amongst other things the picking tool 3 and support 5 in the starting position of the picking tool 3, which starting position is well above the culture dish 4 as is shown in solid lines in FIG. 1. In this starting position the measurement device 10 provided a signal representing the start electrical capacity to the microprocessor 8. In the present embodiment this signal representing the start electrical capacity is the oscillation frequency of the oscillator circuit 18, which frequency can be shown on the display.

When lowering the picking tool 3 towards the culture dish 4 the measurement device 10 continues determining the electrical capacity (i.e. the oscillating frequency) and continuously provides a signal representing the oscillation frequency to the microprocessor 8. The microprocessor comprises a comparator 21 for performing a comparison of the electrical capacity (i.e. the oscillation frequency) during lowering of the picking tool 3 with the start electrical capacity (i.e. the start oscillation frequency). At the moment the picking tool 3' contacts the cell material 12 the capacity of the system changes, which has the immediate result that the oscillation frequency of the oscillation circuit changes. The comparator 21 of the microprocessor 8 detects this change and provides a comparison signal indicative of this change (or comparison), which comparison signal is used by the microprocessor to control the movement of the positioning device 7. In case the oscillation frequency (i.e. the capacity) measured during lowering of the picking tool 3 deviates from the start oscillation frequency, for example when the picking tool 3 contacts the cell material, the controller immediately stops the lowering of the picking tool 3 based on the comparison signal provided by the comparator 21. In this manner it is guaranteed that the picking tool does not penetrate the cell material and only cell material is in contact with the picking tool.

In case the picking tool 3' contacts the cell material 12 the current flowing through the measuring circuit, and thus also through the cell material, is less than 0.1 mA, which is not detrimental to growth of cell material. The current flowing through the measuring circuit is schematically indicated in FIG. 1 by the letter A.

After the picking tool 3 has contacted the cell material 12 and the microprocessor has controlled the positioning device 7 to stop the movement of the picking tool in the direction of the culture dish, the microprocessor 8 controls the positioning device to reverse the movement of the picking tool 3, i.e. to remove the picking tool 3 from the cell material 12.

Although the picking tool 3 with the cell material carried by it, may be directly transferred for further processing, as is known in the art, in the presently most preferred embodiment of the invention, the microprocessor 8 controls the reverse movement of the positioning device 7 such that the picking tool 3 is first removed over a predetermined distance away from the contact position towards a check position (intermediate the start position and the contact position) and held in said check position. In this check position the oscillation frequency (i.e. the electrical capacity) of the measuring circuit, containing the picking tool 3 and the annular support 5 is measured. In case in this check position the determined oscillation frequency deviates from the start oscillation frequency (as determined by the comparator 21) the microprocessor 8 provides a warning signal indicating that there might be a thread of cell material still connecting the picking tool 3 and the cell material 12 on the culture medium. This warning signal may be provided to an operator who can take appropriate actions.

However, since it is desired to automate picking up and transferring cell material as much as possible in the presently most preferred embodiment a picking tool holder 2 is used which is adapted for removably holding the picking tool 3. Thus the picking tool holder 2 is adapted to grasp and release the picking tool 3, e.g. by means of displaceable fingers or any other suitable means. In this manner the warning signal can be used to release the picking tool 3 from the picking tool holder 2 in case the oscillation frequency (i.e. the electrical capacity) measured in the check position differs from the start oscillation frequency (i.e. the start electrical capacity) such that the picking tool 3 falls into the culture dish 4. The culture dish 4 with the picking tool 3 which has been dropped into it can then be discarded by any suitable automated means, which are known per se. In addition when the picking tool holder is adapted to removably hold the picking tool a new picking tool can be used each time cell material has to be picked up from the surface of a culture medium in a culture dish.

The measurement device described above is one of the many measurement devices which can be used to measure the change in capacity when during movement from the starting position towards the culture dish the picking tool contacts the cell material. The present invention is not restricted to a specific device, but any measurement device known to the person skilled in the art can be used within the invention. In addition the positioning device is not described in detail since also for this positioning device any known device suitable for displacing the picking tool in at least the vertical dimension can be used within the invention.

Consequently the assembly as described above generally performs a method for picking up cell material from the surface of a culture medium in a culture dish, which method subsequently comprising the steps of displacing a picking tool towards the cell material, determining contact between the picking tool and the cell material, and removing the picking tool from the cell material thereby picking up cell material, wherein the step of determining contact between the picking tool and the cell material is performed by carrying out capacitive measurements. Lowering of the picking tool is stopped in a contact position when the measured capacity deviates from the start electrical capacity. In case the contact position of the picking tool is measured, this determined position also can be used by the microprocessor to control the operation of the positioning device for moving the picking tool. For example the picking tool can be displaced at different speeds, e.g. a higher speed starting from the starting position and a reduced speed when the picking tool approaches the contact position of a previous cycle. This is possible since it can be assumed that in general the surface of the culture medium is level.

The invention claimed is:

1. Assembly for picking up cell material from the surface of a culture medium in a culture dish, said assembly comprising:
    a picking tool device comprising a picking tool holder of electrically conducting material, said picking tool holder being mounted to the picking tool device in an electrically insulated manner, said picking tool holder holding a picking tool made of electrically conducting material, said picking tool being held by the picking tool holder in an electrically conducting manner, said picking tool being electrically connected to a first electrical lead;
    a culture dish support made of electrically conducting material for supporting the culture dish the support comprising an annular element made of electrically conducting material surrounding a layer of electrically insulating material on which the culture dish can be supported, the annular element being electrically connected to a second electrical lead wherein the culture dish to be placed on the layer of insulating material is also made of an electrically insulating material;
    a positioning device for positioning the picking tool in a starting position above the culture dish and for lowering and raising the picking tool towards and away from the culture dish, respectively such that as the picking tool is displaced toward a cellular material on the culture plate the apparatus measures electrical capacitance wherein the device further comprises:
    a controller for controlling the movement of the positioning device;
    an oscillator circuit connected with the first and second electrical leads and configured to provide a signal representing an oscillation frequency characterized by the electrical capacitance of a measuring circuit that, in operation, comprises the first electrical lead, the picking tool holder, the picking tool, the second electrical lead, the layer of electrically insulating material, the support, and the culture dish;
    said controller comprising a comparator for performing a comparison of the oscillation frequency during lowering of the picking tool with a start oscillation frequency and for providing a comparison signal indicative of said comparison, said controller controlling the movement of the positioning device at least based on the comparison signal and determining contact between the picking tool and the cellular material based on a detected deviation of the oscillation frequency during lowering of the picking tool from the start oscillation frequency.

2. Assembly as claimed in claim 1, wherein the controller is adapted to stop the lowering of the picking tool when, based on the comparison, the comparator signals that the oscillation frequency of the oscillation circuit has changed.

3. Assembly as claimed in claim 1, wherein the picking tool holder is adapted to removably hold a picking tool.

4. Assembly as claimed in claim 1, wherein electrically insulating material is transparent and is interposed between the support and the culture dish.

5. Assembly as claimed in claim 1, wherein the picking tool is made of an electrically conductive plastic material.

* * * * *